United States Patent

Masuzawa et al.

[11] Patent Number: 4,826,982
[45] Date of Patent: May 2, 1989

[54] QUINOLONECARBOXYLIC ACID DERIVATIVES

[75] Inventors: Kuniyoshi Masuzawa, Koga; Seigo Suzue; Keiji Hirai, both of Kuki; Takayoshi Ishizaki, Saitama, all of Japan

[73] Assignee: Kyorin Pharmaceutical Co., Ltd., Tokyo, Japan

[21] Appl. No.: 902,606

[22] Filed: Sep. 2, 1986

[30] Foreign Application Priority Data

Sep. 10, 1985 [JP] Japan .................. 60-200240

[51] Int. Cl.$^4$ ............................ C07D 401/04
[52] U.S. Cl. ........................ 544/363; 546/156; 558/425; 560/38; 560/42; 560/51; 560/53; 560/54; 562/493; 260/544 D; 564/183; 564/218; 564/441; 564/442; 568/938
[58] Field of Search ........................... 544/363

[56] References Cited

U.S. PATENT DOCUMENTS 4,556,658 12/1985 Grohe et al. .................. 544/363
4,599,334 7/1986 Petersen et al. ............... 544/363

FOREIGN PATENT DOCUMENTS 0178388 4/1986 European Pat. Off. ......... 544/363

*Primary Examiner*—Glennon H. Hollrah
*Assistant Examiner*—James H. Turnipseed
*Attorney, Agent, or Firm*—Oblon, Fisher, Spivak, McClelland & Maier

[57] ABSTRACT

Quinolonecarboxylic acid derivatives of the following formula,

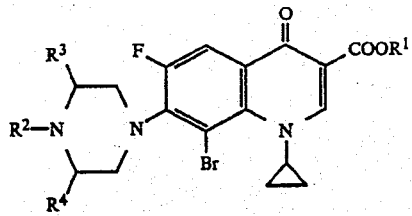

wherein $R^1$, $R^2$, $R^3$ and $R^4$ are each independently hydrogen atom or lower alkyl group; the hydrates or the pharmaceutically acceptable acid addition or alkali salts thereof are useful as an antibacterial agent.

4 Claims, No Drawings

QUINOLONECARBOXYLIC ACID DERIVATIVES

DETAILED DESCRIPTION OF THE INVENTION

This invention is concerned with certain novel useful quinolonecarboxylic acid derivatives, having antibacterial activities, with a process for their preparation, and with compositions containing them.

This invention provides compounds of the formula (I),

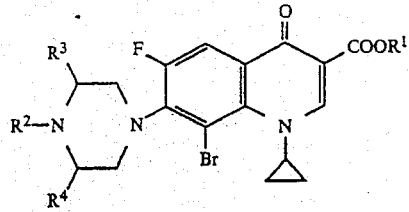

wherein $R^1$, $R^2$, $R^3$ and $R^4$ are each independently hydrogen atom or lower alkyl group; the hydrates or the pharmaceutically acceptable acid addition or alkali salt thereof.

Since nalidixic acid which has been employed for treatment of urinary tract infections by aerobic gram-negative bacteria, was introduced in 1963, intensive work has been carried out on the further development of quinolonecarboxylic acid analogue.

Some compounds such as Norfloxacin have recently been developed which are effective against not only aerobic gram-negative bacteria, but also gram-positive bacteria. However, the activity of these compounds against gram-positive bacteria is fairly less than the activity of the compounds against gram-negative bacteria.

Very recently, some drugs which include 1-ethyl-7-[3-[(ethylamino)methyl]-1-pyrrolidinyl]-6,8-difluoro-1,4-dihydro-4-oxo-3-quinolinecarboxylic acid (CI-934) have been found which exhibit relatively strong activity against gram-positive bacteria. However, these compounds possess weaker activity against gram-negative bacteria than such known compounds as Norfloxacin and Ciprofloxacin.

As a result of an investigation, the present inventors have now unexpectedly found that new derivatives of quinolonecarboxylic acid represented by the formula (I) have excitingly potential activity against gram-positive bacteria without decrease of activity against gram-negative bacteria in comparison with that of any prior-analogue and therefore are superior to commercial preparations and investigational drugs in the in vitro and in vivo antibacterial activity against both gram-negative and gram-positive bacteria.

Furthermore, the compounds of this invention possess excellent antibacterial activity not only against aerobic bacteria but also against anaerobic bacteria and mycoplasmas.

The present compounds are well absorbed and distributed into the tissue when administered orally in animals.

The compounds of this invention, therefore, are active at low doses against both gram-positive and gram-negative bacteria and thus constitute valuable agents for the treatment of infectious human, animal or plant diseases.

The compounds of the formula (I) are synthesized by reacting a compound of the formula (II),

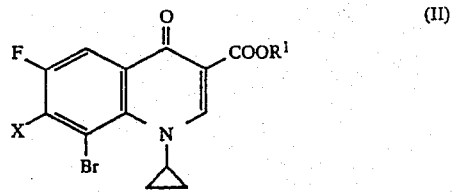

wherein $R^1$ is hydrogen atom or lower alkyl group, X is halogen atom, with a compound of the formula (III),

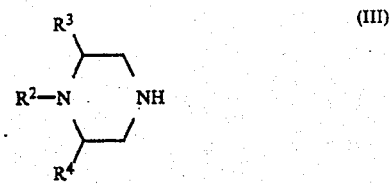

wherein $R^2$, $R^3$ and $R^4$ are the same as defined above. The reaction is carried out by mixing the two reactants in a solvent such as water, alcohols, acetonitrile, dimethylformamide (DMF), dimethyl sulfoxide (DMSO), hexamethyl phosphoric triamide, pyridine, picoline and the like or in absence of the solvent.

The above reaction is carried out at room temperature to 200° C., preferably 60° C. to 160° C., more preferably 60° C. to 120° C. for 1 to several hours. It is desirable that a slight excess (2 to 5 moles) of the compound of the formula (III) is used per mole of the compound of the formula (II) and excess (2 to 10-fold volume) of the solvent is used per volume of the compound of the formula (III).

When R in the formula (II) is lower alkyl group, the reaction product (carboxylic ester) is hydrolyzed to the corresponding carboxylic acid by the usual manner.

The hydrolysis is carried out by treating the compound of formula (I:R is lower alkyl group) with alkali metal hydroxide solution such as sodium hydroxide, potassium hydroxide, or mineral acid such as hydrochloric acid, sulfuric acid in water, aqueous alcohols or an appropriate solvent.

Furthermore, the compounds of the formula (I) can be converted, if desired to the pharmaceutically acceptable salts by treatment with acid or alkali. The acid may be organic or inorganic acids such as, for example, hydrochloric acid, sulfuric acid, phosphoric acid, methanesulfonic acid, acetic acid, oxalic acid and lactic acid. The alkali salts may be, for example, sodium, potassium, magnesium, calcium, aluminum, cerium, chromium, cobalt, copper, iron, zinc, platinum, silver, gold and manganese salts.

The compound of the formula (I) may be used as medicines, which may be, for example, tablets, capsules, powder, ointments, suppositories, injections or eye drops, suitable for peroral, parenteral enteral or local administration.

The starting compound of the formula (II) is also new and obtained, for example, from 3-chloro-4-fluoroaniline via several steps as illustrated in the following chart and in example.

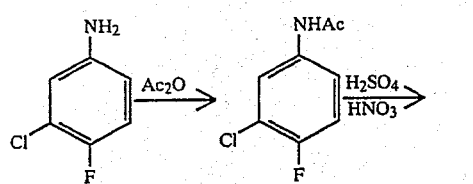

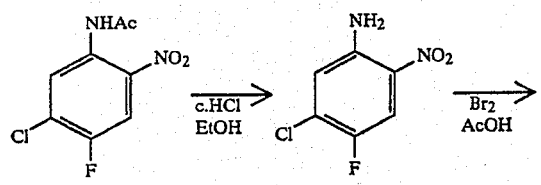

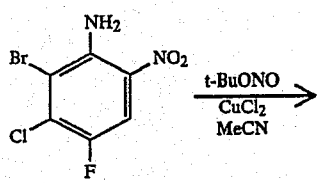

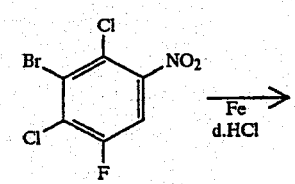

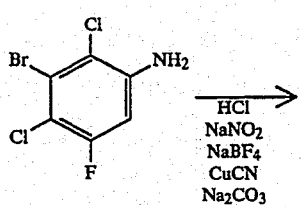

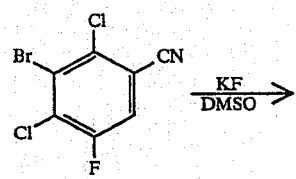

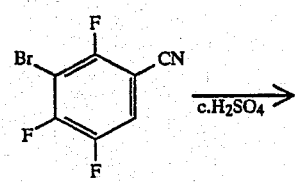

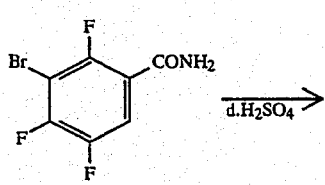

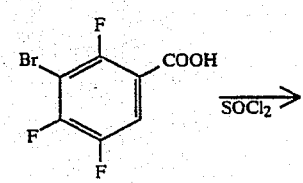

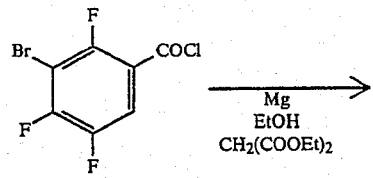

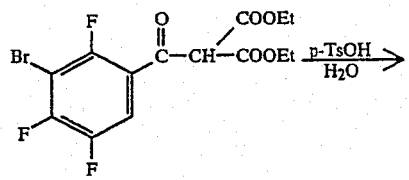

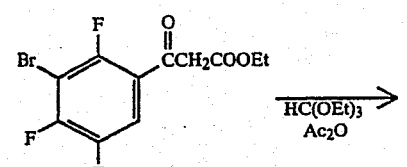

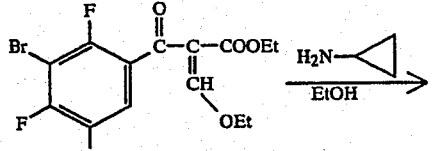

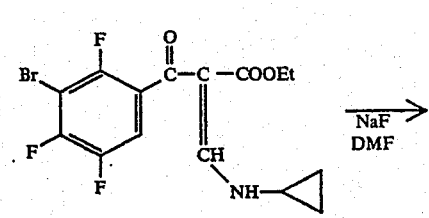

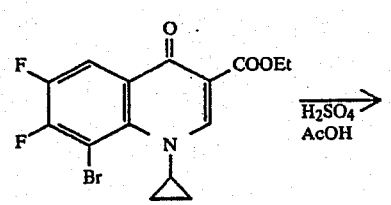

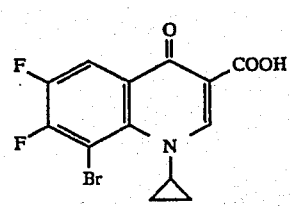

The following example will further illustrate the invention without, however, limiting it thereto.

EXAMPLE 1.

N-(3-Chloro-4-fluorophenyl)acetamide

To 3-chloro-4-fluoroaniline (100 g) was slowly added acetic anhydride (200 ml). After allowed to stand for 30 minutes, the reaction mixture was poured into water (1 litter). The resulting precipitate was collected by filtration and recrystallized from aqueous ethanol to give the title compound (119.4 g), mp 118°–119° C.

EXAMPLE 2.

N-(3-Chloro-4-fluoro-6-nitrophenyl)acetamide

To a solution of N-(3-chloro-4-fluorophenyl)acetamide (55 g) in concentrated sulfuric acid (165 ml) was added dropwise concentrated nitric acid (d 1.42, 154 ml) at 5°–10° C. during an hour with stirring in an ice-salt bath. After stirring for an hour at the same temperature, the reaction mixture was poured into ice water. The resulting precipitate was collected by filtration, sufficiently washed with water and recrystallized from acetonitrile to give the title compound (48.9 g) as yellow needles, mp 114°–115° C.

EXAMPLE 3.

3-Chloro-4-fluoro-6-nitroaniline

A solution of N-(3-chloro-4-fluoro-6-nitrophenyl)acetamide (30 g) in concentrated hydrochloric acid (50 ml) and ethanol (200 ml) was refluxed for 2.5 hours. To the reaction mixture was added ice water (300 ml) and the resulting precipitate was collected by filtration, washed with water and dried to give the title compound (24.9 g) as yellow needles, mp 149.5°–150° C.

Analysis (%) for $C_6H_4ClFN_2O_2$, Calcd. (Found): C, 37.82 (37.85); H, 2.11 (2.03); N, 14.70 (14.80).

EXAMPLE 4.

2-Bromo-3-chloro-4-fluoro-6-nitroaniline

Into a solution of 3-chloro-4-fluoro-6-nitroaniline (200.3 g) in acetic acid (1.5 litter) was added bromine (339 g) during a period of 80 minutes at 50° C. under stirring and stirred for further 2 hours. The reaction mixture was poured into ice water (3 litter) and the resulting precipitate was collected by filtration, washed with water and added to a mixture of concentrated hydrochloric acid (300 ml) and ethanol (1.2 litter). The mixture was refluxed for 8.5 hrs. After cooling, the precipitate was collected by filtration and washed with water and dried. The title compound thus obtained weighed 235.6 g as yellow needles, mp 146°–147° C.

EXAMPLE 5.

3-Bromo-2,4-dichloro-5-fluoronitrobenzene

To a mixture of anhydrous cupric chloride (147 g) and 2-bromo-3-chloro-4-fluoro-6-nitroaniline (235.6 g) in anhydrous acetonitrile (1.5 litter) was added tert-butylnitrite (135.2 g) at 60° C. during 70 minutes. The reaction mixture was poured into ice-chilled diluted hydrochloric acid (1.5 litter) and extracted with benzene. The organic layer was successively washed with ice-chilled diluted hydrochloric acid and water saturated with sodium chloride, dried over anhydrous sodium sulfate and concentrated. The resulting residue was purified by distillation to give the title compound (218.8 g), bp 78°–117° C./2 mmHg. The oil was crystallized from methanol to give yellow prisms, mp 65.5°–67.5° C.

EXAMPLE 6.

3-Bromo-2,4-dichloro-5-fluoroaniline

To a suspension of iron powder (135.4 g) in water (140 ml), with vigorous stirring at 50°–60° C., was slowly added concentrated hydrochloric acid (18 ml). After ethanol (350 ml) was mixed, 3-bromo-2,4-dichloro-5-fluoronitrobenzene (218.8 g) was added portionwise to the suspension at 52°–76° C. during an hour. After stirring for 75 minutes at the same temperature, the hot reaction mixture was filtered after adding benzene (500 ml) and the insoluble material was successively washed with hot ethanol (100 ml) and benzene (200 ml). The filtrate and washings were combined. The organic layers were washed with water saturated with sodium chloride, dried over anhydrous sodium sulfate and then concentrated. The resulting residue was recrystallized from ethanol-water to give the title compound (141.6 g) as light brown needles, mp 126°–129.5° C.

EXAMPLE 7.

3-Bromo-2,4-dichloro-5-fluorobenzonitrile

To a suspension of 3-bromo-2,4-dichloro-5-fluoroaniline (141.6 g) in concentrated hydrochloric acid (900 ml) with vigorous stirring was added sodium nitrite (56.6 g) in water (120 ml) at −2°∼0° C. for 40 minutes. After stirred for 30 minutes, the mixture was poured into ice water (700 ml) containing sodium tetrafluoroborate (180 g), stirred vigorously for 20 minutes and then allowed to stand for 15 minutes in an ice bath. The resulting precipitate was collected by filtration and washed with chilled water. The wet crude tetrafluoroborate thus obtained weighed 270.8 g. The borate was added portionwise during 45 minutes to a solution of cuprous cyanide (98 g), potassium cyanide (142.4 g) and sodium carbonate (29 g) in water (800 ml) with vigorous stirring at 9°–10° C. After the mixture was stirred for 2 hours at room temperature, benzene (700 ml) and potassium cyanide (71 g) were added to the suspension and then the mixture was stirred for 30 minutes. The insoluble material was collected by filtration, and washed with benzene (300 ml×2). The filtrate and washings were combined and washed five times with water saturated with sodium chloride, dried over anhydrous sodium sulfate and then concentrated. The resulting residue was recrystallized from ethanol to give the title compound (75.5 g) as red brown prisms, mp 110.5°–112.5° C.

EXAMPLE 8.

3-Bromo-2,4,5-trifluorobenzonitrile

To a solution of potassium fluoride (123 g) in dimethyl sulfoxide (400 ml) with stirring at 133° C. was added 3-bromo-2,4-dichloro-5-fluorobenzonitrile (68.4 g) and then the mixture was stirred for 5 hours and 20 minutes at 130° C. After cooling, the reaction mixture was poured into ice water (1 litter) and extracted with benzene. The organic layer was washed with water saturated with sodium chloride, dried over anhydrous sodium sulfate and distilled to give the title compound (15.7 g) as colorless oil, bp 82.5° C./13 mmHg–80.0° C./1 mmHg.

EXAMPLE 9.

3-Bromo-2,4,5-trifluorobenzoic acid

A mixture of 3-bromo-2,4,5-trifluorobenzonitrile (13.9 g) in concentrated sulfuric acid (8 ml) was heated for 20 minutes on an oil bath (100° C.), poured into ice water (350 ml). The resulting precipitate was collected by filtration and washed with water. The filtrate and washings were extracted 3 times with dichloromethane. The dichloromethane layer was washed with water saturated with sodium chloride, dried over anhydrous sodium sulfate and concentrated to give the residue.

The combined mixture of the precipitate obtained previously and the residue was purified by silica gel chromatography eluting with dichloromethane dichloromethane:methanol (10:1) to give 3-bromo-2,4,5-trifluorobenzamide (8.7 g).

A mixture of 3-bromo-2,4,5-trifluorobenzamide (8.7 g) and 18N-sulfuric acid (50 ml) was stirred at 100° C. for 4 hours, and then poured into ice water (200 ml). The resulting precipitate was collected by filtration and recrystallized from dichloro-methane-n-hexane to give the title compound (6.9 g), mp 125°-127° C.

EXAMPLE 10.

3-Bromo-2,4,5-trifluorobenzoyl chloride

A solution of the 3-bromo-2,4,5-trifluorobenzoic acid (2.5 g) in thionyl chloride (10 ml) was refluxed for 2.5 hours, and then concentrated. The resulting residue was purified by distillation through Widmer fractionating column to give the title compound (2.3 g), bp 98°-102° C./18 mmHg.

EXAMPLE 11.

Diethyl 3-bromo-2,4,5-trifluorobenzoylmalonate

Magnesium turnings (0.22 g) and carbon tetrachloride (0.1 ml) was added to absolute ethanol (1.5 ml). To the stirring suspension was added dropwise a solution of diethyl malonate (1.4 g) and absolute ethanol (2 ml) in toluene (6 ml) during 25 minutes at 50°-60° C. The mixture was stirred for 40 minutes, and then cooled. A solution of 3-bromo-2,4,5-trifluorobenzoyl chloride (2.27 g) in anhydrous toluene (3 ml) was added dropwise to the solution at $-8°\sim-4.5°$ C. during 28 minutes. The mixture was stirred for 2 hours and then mixed with ice-chilled diluted sulfuric acid. The resulting organic layer was collected and the water layer was extracted with toluene (6 ml×4). The combined organic layer was washed with water, dried over anhydrous sodium sulfate and then concentrated to give the title compound (3.25 g) as pale yellow oil.

EXAMPLE 12.

Ethyl 3-bromo-2,4,5-trifluorobenzoylacetate

To an emulsion of diethyl 3-bromo-2,4,5-trifluorobenzoylmalonate (3.25 g) in water (4 ml) was added p-toluenesulfonic acid (4 mg) and refluxed for 3 hours with vigorous stirring. After cooling, the reaction mixture was extracted with dichloromethane (8 ml×4). The organic layer was washed with water saturated with sodium chloride, dried over anhydrous sodium sulfate and concentrated. The residue was recrystallized from dichloromethane-n-hexane to give the title compound (1.51 g), mp 85°-88° C.

EXAMPLE 13.

Ethyl 2-(3-bromo-2,4,5-trifluorobenzoyl)-3-ethoxyacrylate

A mixture of ethyl 3-bromo-2,4,5-trifluorobenzoylacetate (1.5 g), ethyl orthoformate (1.0 g) and acetic anhydride (1.2 g) was stirred at 130° C. for 4.5 hours and then concentrated to give the title compound (1.75 g) as yellow oil.

EXAMPLE 14.

Ethyl 2-(3-bromo-2,4,5-trifluorobenzoyl)-3-cyclopropylaminoacrylate

To a solution of ethyl 2-(3-bromo-2,4,5-trifluorobenzoyl)-3-ethoxyacrylate (1.75 g) in absolute ethanol (5 ml) was added a solution of cyclopropylamine (0.32 g) in absolute ethanol (2 ml) under ice-cooling during 30 minutes. The mixture was stirred at 5°-20° C. for 2.5 hours and concentrated. The residue was recrystallized from petroleum ether to give the title compound (1.36 g), mp 74°-76° C.

EXAMPLE 15.

Ethyl 8-bromo-1-cyclopropyl-6,7-difluoro-1,4-dihydro-4-oxo-3-quinolinecarboxylate To a solution of ethyl 2-(3-bromo-2,4,5-trifluorobenzoyl)-3-cyclopropylaminoacrylate (1.35 g) in anhydrous dimethylformamide (5 ml) was added sodium fluoride (0.23 g). The mixture was stirred at 97°-108° C. for 7.5 hours, and then poured into ice water (50 ml) and the resulting precipitate was collected by filtration, washed with water and recrystallized from dichloromethane-n-hexane to give the title compound (1.05 g), mp 163.5°-168° C. as colorless prisms.

NMR (δ in CDCl₃), 1.0–1.4 (4H, m,

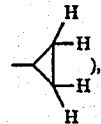

), 1.40 (3H, t, J=7.3 Hz, —CH₂<u>CH₃</u>), 4.1–4.3 (1H, m,

), 4.39 (2H, q, J=7.2 Hz, —<u>CH₂</u>CH₃), 8.26 (1H, dd, J=9.7, 8.4 Hz, 5-H), 8.68 (1H, s, 2-H).

IR (KBr, cm⁻¹), 1730 (COO), 1600 (CO), 1450, 1310, 1270, 1230, 1200, 1170, 1070, 1030, 860, 800.

EXAMPLE 16.

8-Bromo-1-cyclopropyl-6,7-difluoro-1,4-dihydro-4-oxo-3-quinolinecarboxylic acid

A mixture of ethyl 8-bromo-1-cyclopropyl-6,7-difluoro-1,4-dihydro-4-oxo-3-quinolinecarboxylate (1.0 g), acetic acid (4 ml), water (3 ml) and concentrated sulfuric acid (0.5 ml) was heated on an oil bath (90°-100° C.) for an hour under stirring, then for an hour at room temperature and poured into ice water (20 ml). The resulting precipitate was collected by filtration and washed with water to give the title compound (0.82 g), mp 224°-225.5° C.

NMR (δ in CDCl₃), 1.0–1.5 (4H, m,

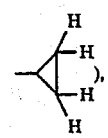

), 4.3–4.5 (1H, m,

8.30 (1H, dd, J=9.2, 8.4 Hz, 5-H), 8.96 (1H, s, 2-H), 13.97 (1H, s-br, —COOH).

IR (KBr, cm$^{-1}$), 2700 (COOH), 1720 (COO), 1610 (CO), 1560, 1450, 1320, 1310, 1260, 1090, 1070, 1040, 1020, 880, 870, 850, 830, 810, 800, 730.

EXAMPLE 17.

8-Bromo-1-cyclopropyl-6-fluoro-1,4-dihydro-4-oxo-7-(1-piperazinyl)-3-quinolinecarboxylic acid and its hydrochloride 8-Bromo-1-cyclopropyl-6,7-difluoro-1,4-dihydro-4-oxo-3-quinolinecarboxylic acid (0.2 g) was added to the solution of anhydrous piperazine (0.25 g) in anhydrous DMSO (2.5 ml) and stirred at 65°–78° C. (bath temperature) for 4.5 hours. After the reacting mixture was concentrated under reduced pressure, the resulting residue was added water and the resulting precipitate was collected by filtration. This precipitate was recrystallized from the mixture of dichloromethane-methanol to give the title compound (20 mg) as pale yellow prisms, mp 222°–226° C. (decompd.).

Analysis (%) for $C_{17}H_{17}BrFN_3O_3 \cdot H_2O$, Calcd. (Found): C, 47.68 (47.88); H, 4.47 (4.20); N, 9.81 (9.66).

After addition of concentrated hydrochloric acid (several drops) to the above mother liquor, the resulting precipitate was collected by filtration and washed with water to give its hydrochloride (20 mg) as pale yellow prisms, mp 300° C. (decompd.).

Analysis (%) for $C_{17}H_{17}BrFN_3O_3 \cdot HCl \cdot 7/3\ H_2O$, Calcd. (Found): C, 41.78 (41.81); H, 4.67 (4.21); N, 8.60 (8.51).

EXAMPLE 18.

8-Bromo-1-cyclopropyl-6-fluoro-1,4-dihydro-7-(3-methyl-1-piperazinyl)-4-oxo-3-quinolinecarboxylic acid hydrochloride 8-Bromo-1-cyclopropyl-6,7-difluoro-1,4-dihydro-4-oxo-3-quinolinecarboxylic acid (0.2 g) was added to the solution of 2-methylpiperazine (0.24 g) in anhydrous DMSO (2.5 ml) and stirred at 65°–78° C. (bath temperature) for 4.5 hours. After the reacting mixture was concentrated under reduced pressure, the resulting residue was added water and the resulting precipitate was filtered off. After addition of concentrated hydrochloric acid (several drops) to the mother liquor, the resulting precipitate was collected by filtration and washed with water to give the title compound (20 mg) as pale yellow prisms, mp 300° C. (decompd.).

Analysis (%) for $C_{18}H_{19}BrFN_3O_3 \cdot HCl \cdot 4/3\ H_2O$, Calcd. (Found): C, 44.60 (44.46); H, 4.71 (4.40); N, 8.67 (8.48).

EXPERIMENT 1.

Antibacterial spectrum

Minimal inhibitory concentrations (MICs) were determined in accordance with the method recommended by Japan Society of Chemotherapy. The results are shown in Table 1.

TABLE 1

| | | In vitro antibacterial activity (standard strains) | | | |
|---|---|---|---|---|---|
| | | MIC (μg/ml) | | | |
| Organism (10$^6$ cells/ml) | Gram | Exp. 17 | Exp. 18 | CPFX | OFLX |
| Bacillus subtilis PCI 219 | + | 0.05 | 0.05 | 0.025 | 0.10 |
| Staphylococcus aureus 209 P | + | 0.10 | 0.10 | 0.20 | 0.20 |
| S. aureus IID 670 (Terajima) | + | 0.20 | 0.20 | 0.20 | 0.39 |
| S. epidermidis IID 866 | + | 0.20 | 0.20 | 0.20 | 0.39 |
| Streptococcus pyogenes (S-8) | + | 0.39 | 0.78 | 0.39 | 1.56 |
| S. pyogenes IID 692 | + | 0.78 | 0.78 | 0.78 | 3.13 |
| S. pneumoniae IID 552 | + | 0.78 | 0.78 | 0.78 | 1.56 |
| E. faecalis IID 682 | + | 0.39 | 0.78 | 0.78 | 1.56 |
| Escherichia coli NIHJ JC-2 | − | 0.0125 | 0.0125 | ≦0.0063 | ≦0.025 |
| E. coli ATCC 10536 | − | 0.025 | 0.025 | 0.0125 | 0.05 |
| Proteus vulgaris IFO 3167 | − | 0.025 | 0.025 | 0.0125 | 0.05 |
| P. mirabilis IID 994 | − | 0.025 | 0.025 | 0.0125 | 0.05 |
| Morganella morganii IID 602 | − | 0.05 | 0.10 | 0.25 | 0.10 |
| Klebsiella pneumoniae KY(GN)6445 | − | 0.025 | 0.05 | 0.0125 | 0.05 |
| K. pneumoniae 1-220S | − | 0.05 | 0.10 | 0.05 | 0.20 |
| Enterobacter cloacae IID 977 | − | 0.05 | 0.10 | 0.025 | 0.10 |
| Citrobacter freundii IID 976 | − | 0.025 | 0.05 | 0.0125 | 0.10 |
| Serratia marcescens IID 618 | − | 0.05 | 0.10 | 0.025 | 0.10 |
| Shigella sonnei IID 969 | − | 0.025 | 0.025 | 0.0063 | 0.05 |
| Salmonella enteritidis IID 604 | − | 0.025 | 0.05 | 0.0125 | 0.10 |
| Pseudomonas aeruginosa V-1 | − | 0.39 | 0.39 | 0.05 | 0.39 |
| P. aeruginosa IFO 12689 | − | 0.78 | 3.13 | 0.39 | 3.13 |
| Yersinia enterocolitica IID 981 | − | 0.05 | 0.10 | 0.025 | 0.20 |
| Acinetobacter anitratus IID 876 | − | 0.10 | 0.05 | 0.20 | 0.20 |
| Alcaligenes faecalis 0114002 | − | 0.20 | 0.39 | 0.39 | 0.78 |
| Bacteroides fragilis GM 7000 | − | 0.78 | 0.78 | 6.25 | 3.13 |
| B. fragilis 0558 | − | 0.78 | 0.39 | 3.13 | 1.56 |
| B. fragilis 25285 | − | 0.78 | 0.39 | 6.25 | 1.56 |
| B. distasonis 8503 | − | 1.56 | 1.56 | 6.25 | 6.25 |
| B. thetaiotaomicron (0661) | − | 1.56 | 1.56 | 12.5 | 6.25 |
| Fusobacterium necrophorum S-45 | − | 0.78 | 0.78 | 1.56 | 1.56 |
| F. varium KYA 8501 | − | 3.13 | 3.13 | 25 | 12.5 |
| Eubacterium lentum GAI 5242 | + | 0.39 | 0.39 | 0.78 | 0.78 |
| Propionibacterium acens 11828 | + | 6.25 | 6.25 | 12.5 | 12.5 |
| Peptococcus magnus KY 017 | + | 0.39 | 0.39 | 0.39 | 0.78 |
| Clostridium perfringens KYA 13123 | + | 0.78 | 0.78 | 0.39 | 0.78 |
| C. ramosum | + | 6.25 | 6.25 | 12.5 | 12.5 |

TABLE 1-continued

| | | In vitro antibacterial activity (standard strains) | | | |
| --- | --- | --- | --- | --- | --- |
| | | MIC (μg/ml) | | | |
| Organism ($10^6$ cells/ml) | Gram | Exp. 17 | Exp. 18 | CPFX | OFLX |
| *Peptostreptococcus anaerobius* KYA 27337 | + | 1.56 | 1.56 | 1.56 | 3.13 |
| *Pst. micros* UPI 5464-1 | + | 0.39 | 0.39 | 0.20 | 0.78 |
| *Veillonella parvula* KYA 10790 | − | 0.39 | 0.39 | 0.20 | 0.78 |

CPFX: ciprofloxacin
OFLX: ofloxacin

What is claimed is:

1. A compound of the formula (I);

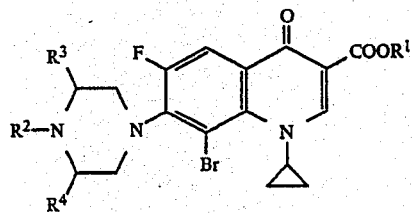

(I)

wherein $R^1$, $R^2$, $R^3$ and $R^4$ are each independently hydrogen or lower alkyl; the hydrates or the pharmaceutically acceptable acid addition or alkali salts thereof.

2. The compound of claim 1, wherein said compound is 8-bromo-1-cyclopropyl-6-fluoro-1,4-dihydro-4-oxo-7-(1-piperazinyl)-3-quinolinecarboxylic acid.

3. The compound of claim 1, wherein said compound is 8-bromo-1-cyclopropyl-6-fluoro-1,4-dihydro-7-(3-methyl-1-piperazinyl)-4-oxo-3-quinolinecarboxylic acid hydrochloride.

4. An antibacterial pharmaceutical composition, which comprises:
an antibacterially effective amount of the compound of claim 1 in combination with a pharmaceutically acceptable carrier.

* * * * *